US006986752B2

(12) United States Patent
McGuckin, Jr. et al.

(10) Patent No.: US 6,986,752 B2
(45) Date of Patent: Jan. 17, 2006

(54) PERITONEAL DIALYSIS CATHETER AND INSERTION METHOD

(75) Inventors: James F. McGuckin, Jr., Radnor, PA (US); Paul Tashjian, King of Prussia, PA (US); Peter W. J. Hinchliffe, Downington, PA (US)

(73) Assignee: Rex Medical, LP, Conshohocken, PA (US)

( * ) Notice: Subject to any disclaimer, the term of this patent is extended or adjusted under 35 U.S.C. 154(b) by 418 days.

(21) Appl. No.: 10/057,022

(22) Filed: Jan. 25, 2002

(65) Prior Publication Data

US 2002/0091352 A1     Jul. 11, 2002

Related U.S. Application Data

(63) Continuation-in-part of application No. 10/025,506, filed on Dec. 19, 2001, now Pat. No. 6,814,718, and a continuation-in-part of application No. 10/025,505, filed on Dec. 19, 2001, now Pat. No. 6,858,019.

(60) Provisional application No. 60/326,905, filed on Oct. 3, 2001, provisional application No. 60/260,592, filed on Jan. 9, 2001.

(51) Int. Cl.
*A61M 1/00* (2006.01)

(52) U.S. Cl. .................... 604/29; 604/165.02
(58) Field of Classification Search ............. 604/524, 604/528, 264, 29, 165.02, 164.01, 164.06, 604/170.03, 44, 164.13
See application file for complete search history.

(56) References Cited

U.S. PATENT DOCUMENTS 1,248,492 A * 12/1917 Hill ..................... 604/165.02
2,460,473 A    2/1949 Larkin et al.

(Continued)

FOREIGN PATENT DOCUMENTS

EP           0301854         2/1989

(Continued)

OTHER PUBLICATIONS

Moureau, Modified Seldinger Insertion Technique for PICC Insertion: The New Wave for Nurses.

(Continued)

*Primary Examiner*—Sharon Kennedy
(74) *Attorney, Agent, or Firm*—Neil D. Gershon (57) ABSTRACT

A peritoneal dialysis catheter for insertion into the abdominal cavity of a patient for delivering and withdrawing fluid from a patient comprising a catheter body having a proximal portion, a distal tip portion and a first longitudinally extending lumen configured to deliver fluid into the abdominal cavity. First and second side openings are formed in an outer wall of the catheter body adjacent the distal tip portion and are in fluid communication with the first lumen and configured for passage of fluid therethrough. A stiffening insert is positioned in the distal tip portion and has a first stiffness greater than a second stiffness of the distal tip portion to facilitate entry into the abdominal cavity. The stiffening insert has a lumen therethrough communicating with the first lumen. A method for insertion of the dialysis catheter is also disclosed.

16 Claims, 6 Drawing Sheets

U.S. PATENT DOCUMENTS

| | | | | |
|---|---|---|---|---|
| 3,680,562 A | * | 8/1972 | Wittes et al. | 604/500 |
| 3,833,003 A | | 9/1974 | Tarricco | |
| 3,938,530 A | | 2/1976 | Santomieri | |
| 4,134,402 A | | 1/1979 | Mahurkar | |
| 4,270,535 A | | 6/1981 | Bogue et al. | |
| 4,403,983 A | | 9/1983 | Edelman et al. | |
| 4,406,656 A | | 9/1983 | Hattler et al. | |
| 4,432,752 A | | 2/1984 | Marlon | |
| 4,451,252 A | | 5/1984 | Martin | |
| 4,479,792 A | * | 10/1984 | Lazarus et al. | 604/29 |
| 4,493,696 A | | 1/1985 | Uldall | |
| 4,543,087 A | | 9/1985 | Sommercorn et al. | |
| 4,545,373 A | | 10/1985 | Christoudias | |
| 4,568,329 A | | 2/1986 | Mahurkar | |
| 4,581,012 A | | 4/1986 | Brown et al. | |
| 4,583,968 A | | 4/1986 | Mahurkar | |
| 4,619,643 A | | 10/1986 | Bai | |
| 4,623,327 A | | 11/1986 | Mahurkar | |
| 4,643,711 A | | 2/1987 | Bates | |
| 4,668,221 A | | 5/1987 | Luther | |
| 4,670,009 A | | 6/1987 | Bullock | |
| 4,682,978 A | | 7/1987 | Martin | |
| 4,717,379 A | | 1/1988 | Ekholmer | |
| 4,738,667 A | | 4/1988 | Galloway | |
| 4,769,016 A | | 9/1988 | Labianca | |
| 4,776,841 A | | 10/1988 | Catalano | |
| 4,808,155 A | | 2/1989 | Mahurkar | |
| 4,808,163 A | | 2/1989 | Laub | |
| 4,832,687 A | | 5/1989 | Smith | |
| 4,842,582 A | | 6/1989 | Mahurkar | |
| 4,894,057 A | | 1/1990 | Howes | |
| 4,895,561 A | | 1/1990 | Mahurkar | |
| 4,927,418 A | | 5/1990 | Dake et al. | |
| 4,950,259 A | | 8/1990 | Geary et al. | |
| 4,961,809 A | | 10/1990 | Martin | |
| 4,968,307 A | | 11/1990 | Dake et al. | |
| 4,994,027 A | | 2/1991 | Farrell | |
| 5,009,636 A | | 4/1991 | Wortley et al. | |
| 5,021,044 A | | 6/1991 | Sharkawy | |
| 5,053,004 A | | 10/1991 | Markel et al. | |
| 5,053,023 A | | 10/1991 | Martin | |
| 5,057,073 A | | 10/1991 | Martin | |
| 5,057,075 A | * | 10/1991 | Moncrief et al. | 604/500 |
| 5,059,170 A | | 10/1991 | Cameron | |
| 5,098,413 A | * | 3/1992 | Trudell et al. | 604/530 |
| 5,122,125 A | | 6/1992 | Deuss | |
| 5,135,599 A | | 8/1992 | Martin et al. | |
| 5,139,486 A | | 8/1992 | Moss | |
| 5,156,592 A | | 10/1992 | Martin et al. | |
| 5,167,623 A | | 12/1992 | Cianci et al. | |
| 5,171,216 A | | 12/1992 | Dasse et al. | |
| 5,195,962 A | | 3/1993 | Martin et al. | |
| 5,207,648 A | | 5/1993 | Gross | |
| 5,207,650 A | | 5/1993 | Martin | |
| 5,209,723 A | | 5/1993 | Twardowski et al. | |
| 5,209,742 A | | 5/1993 | Venema et al. | |
| 5,215,527 A | | 6/1993 | Beck et al. | |
| 5,221,255 A | | 6/1993 | Mahurkar et al. | |
| 5,221,256 A | | 6/1993 | Mahurkar | |
| 5,234,438 A | | 8/1993 | Semrad | |
| 5,246,430 A | | 9/1993 | MacFarlane | |
| 5,273,527 A | | 12/1993 | Schatz et al. | |
| 5,279,596 A | | 1/1994 | Castaneda et al. | |
| 5,346,471 A | | 9/1994 | Raulerson | |
| 5,348,536 A | | 9/1994 | Young et al. | |
| 5,350,358 A | | 9/1994 | Martin | |
| 5,360,397 A | | 11/1994 | Pinchuk | |
| 5,364,344 A | | 11/1994 | Beattie et al. | |
| 5,374,245 A | | 12/1994 | Mahurkar | |
| 5,378,230 A | | 1/1995 | Mahurkar | |
| 5,380,276 A | | 1/1995 | Miller et al. | |
| 5,380,290 A | | 1/1995 | Makower et al. | |
| 5,382,238 A | | 1/1995 | Abrahamson et al. | |
| 5,395,316 A | | 3/1995 | Martin | |
| 5,403,291 A | | 4/1995 | Abrahamson | |
| 5,405,320 A | | 4/1995 | Twardowski et al. | |
| 5,405,341 A | | 4/1995 | Martin | |
| 5,451,206 A | | 9/1995 | Young | |
| 5,472,417 A | | 12/1995 | Martin et al. | |
| 5,480,380 A | | 1/1996 | Martin | |
| 5,486,159 A | | 1/1996 | Mahurkar | |
| 5,489,278 A | | 2/1996 | Abrahamson | |
| 5,509,897 A | | 4/1996 | Twardowski et al. | |
| 5,509,900 A | | 4/1996 | Kirkman | |
| 5,542,925 A | | 8/1996 | Orth | |
| 5,556,390 A | | 9/1996 | Hicks | |
| 5,569,182 A | | 10/1996 | Twardowski et al. | |
| 5,571,093 A | | 11/1996 | Cruz et al. | |
| 5,662,606 A | | 9/1997 | Cimino et al. | |
| 5,693,030 A | * | 12/1997 | Lee et al. | 604/117 |
| 5,713,849 A | | 2/1998 | Bosma et al. | |
| 5,718,678 A | | 2/1998 | Fleming, III | |
| 5,752,939 A | | 5/1998 | Makoto | |
| 5,792,123 A | | 8/1998 | Ensminger | |
| 5,797,869 A | | 8/1998 | Martin et al. | |
| 5,807,311 A | | 9/1998 | Palestrant | |
| 5,807,329 A | | 9/1998 | Gelman | |
| 5,810,789 A | | 9/1998 | Powers et al. | |
| 5,830,196 A | | 11/1998 | Hicks | |
| 5,882,347 A | | 3/1999 | Mouris-Laan et al. | |
| 5,911,715 A | | 6/1999 | Berg et al. | |
| 5,913,848 A | | 6/1999 | Luther et al. | |
| 5,916,208 A | | 6/1999 | Luther et al. | |
| 5,919,160 A | | 7/1999 | Sanfilippo | |
| 5,947,953 A | | 9/1999 | Ash et al. | |
| 5,957,893 A | | 9/1999 | Luther et al. | |
| 5,961,486 A | | 10/1999 | Twardowski et al. | |
| 5,976,103 A | | 11/1999 | Martin | |
| 5,976,120 A | | 11/1999 | Chow et al. | |
| 5,984,908 A | | 11/1999 | Davis et al. | |
| 5,989,206 A | | 11/1999 | Prosl et al. | |
| 6,001,079 A | | 12/1999 | Pourchez | |
| 6,036,654 A | | 3/2000 | Quinn et al. | |
| 6,059,771 A | | 5/2000 | Balbierz et al. | |
| 6,106,540 A | | 8/2000 | White et al. | |
| 6,120,494 A | | 9/2000 | Jonkman | |
| 6,126,631 A | | 10/2000 | Loggie | |
| 6,132,405 A | * | 10/2000 | Nilsson et al. | 604/264 |
| 6,146,354 A | | 11/2000 | Beil | |
| 6,146,373 A | | 11/2000 | Cragg et al. | |
| 6,152,909 A | | 11/2000 | Bagaoisan et al. | |
| 6,156,016 A | | 12/2000 | Maginot | |
| 6,180,059 B1 | | 1/2001 | Divino, Jr. et al. | |
| 6,190,349 B1 | | 2/2001 | Ash et al. | |
| 6,190,371 B1 | | 2/2001 | Maginot et al. | |
| 6,193,685 B1 | | 2/2001 | Goodin | |
| 6,196,996 B1 | | 3/2001 | Teirstein | |
| 6,210,365 B1 | | 4/2001 | Afzal | |
| 6,223,070 B1 | * | 4/2001 | Chait | 600/433 |
| 6,264,627 B1 | | 7/2001 | Liska et al. | |
| 6,273,879 B1 | | 8/2001 | Keith et al. | |
| 6,280,423 B1 | | 8/2001 | Davey et al. | |
| 6,293,927 B1 | | 9/2001 | McGuckin, Jr. | |
| 6,293,958 B1 | | 9/2001 | Berry et al. | |
| 6,296,631 B2 | | 10/2001 | Chow | |
| 6,328,730 B1 | | 12/2001 | Harkrider, Jr. | |
| 6,358,229 B1 | * | 3/2002 | Tihon | 604/170.03 |
| 6,361,529 B1 | | 3/2002 | Goodin et al. | |
| 6,394,141 B2 | | 5/2002 | Wages et al. | |
| 6,454,997 B1 | | 9/2002 | Divino, Jr. et al. | |
| 6,638,242 B2 | | 10/2003 | Wilson et al. | |
| 6,890,321 B2 | | 5/2005 | Luther et al. | |
| 2002/0087145 A1 | | 7/2002 | Ehwald et al. | |
| 2003/0023198 A1 | | 1/2003 | Twardowski | |

| | | | |
|---|---|---|---|
| 2003/0088213 | A1 | 5/2003 | Schweikert |
| 2003/0153898 | A1 | 8/2003 | Schon et al. |
| 2003/0204179 | A1 | 10/2003 | Davey et al. |
| 2004/0064086 | A1 | 4/2004 | Gottlieb et al. |

FOREIGN PATENT DOCUMENTS

| | | |
|---|---|---|
| EP | 0440992 | 8/1991 |
| WO | WO 9737699 | 10/1997 |
| WO | WO 0176677 | 10/2001 |

OTHER PUBLICATIONS

Seldinger Technique for Introducing Catheters.
Journal of Vascular and Interventional Radiology 12:376-378 (2001), Sheathless Technique of Ash Split-Cath Insertion, Aalpen Patel, MD, Stephen Hofkin, MD, David Ball, DO, Gary Cohen, MD and Douglas C. Smith, MD.

* cited by examiner

FIG_8

FIG_9

FIG_10

FIG_11

FIG_12

FIG_13A

FIG_13B

PERITONEAL DIALYSIS CATHETER AND INSERTION METHOD

This application claims priority from provisional application Ser. No. 60/326,905, filed Oct. 3, 2001 and is a continuation-in-part of application Ser. No. 10/025,505, now U.S. Pat. No. 6,858,019 filed Dec. 19, 2001 and application Ser. No. 10/025,506, nou U.S. Pat. No. 6,814,718, filed Dec. 19, 2001, both of which claim priority from provisional application Ser. No. 60/260,592 filed Jan. 9, 2001. The entire contents of each of these application is incorporated herein by reference.

BACKGROUND

1. Technical Field

This application relates to a catheter and more particularly to a peritoneal dialysis catheter and method of insertion.

2. Background of Related Art

The kidneys are organs which function to extract water and urea, mineral salts, toxins, and other waste products from the blood with filtering units called nephrons. From the nephrons the collected waste is sent to the bladder for excretion. For patients having one or both defective kidneys, the dialysis procedure is life saving because it simulates the function of the kidneys.

Dialysis is a process of diffusing blood across a semi-permeable membrane to remove toxic materials and to maintain fluid, electrolyte and acid based balance in patients having impaired kidney function. Hemodialysis is one well known method of providing renal (kidney) function by circulating blood. Peritoneal dialysis is another known method for cleansing the blood.

In the hemodialysis procedure, blood is withdrawn from the patient's body through a catheter or tube and transported to a dialysis machine, also commonly referred to as a kidney machine. The catheter is typically inserted through the jugular vein and maneuvered into position through the superior vena cava into the right atrium to provide high blood flow. In the dialysis machine, toxins and other waste products diffuse through a semi-permeable membrane into a dialysis fluid closely matching the chemical composition of the blood. The filtered blood, i.e. with the waste products removed, is then returned to the patient's body. In some instances, the catheter may be left in place for as long as sixty days. As can be appreciated, proper access to the patient's blood and transport of the blood to and from the dialysis machine for this extended period of time is critical to hemodialysis.

In peritoneal dialysis, removal of toxic substances is achieved by perfusing chemical solutions (dialysate fluid) through the peritoneal cavity. A catheter is inserted into the patient's abdomen (peritoneal cavity) to deliver dialysate fluid to fill the cavity. The peritoneum, the membrane which lines the abdominal cavity, allows chemical wastes and excess water to diffuse out of the blood and pass into the dialysate fluid, as blood vessels in the peritoneal membrane are exposed to the fluid. Thus, waste products move through the pores in the peritoneal membrane and pass into the dialysate fluid. The catheter then drains the dialysate fluid and waste.

Typically, peritoneal dialysis catheters are inserted as follows:

1. an introducer needle is inserted through a first incision;
2. a guidewire is inserted through the introducer needle into the internal abdominal cavity;
3. the introducer needle is withdrawn leaving the guidewire in place;
4. a tear away sheath and dilator are inserted over the guidewire and through the first incision site to provide an access port for the dialysis catheter into the abdominal cavity;
5. the dilator and guidewire are removed, leaving the tear away sheath in place in the first incision which has been expanded by the dilator;
6. the dialysis catheter is inserted through the tear away sheath and advanced into the peritoneal cavity;
7. the sheath is separated, i.e. split, by pulling the tabs apart, and then pulled upwardly away from the dialysis catheter and removed from the body, leaving the catheter in place;
8. a trocar or tunneling tip is attached to the proximal end of the catheter;
9. the trocar and dialysis catheter are pushed through the tissue to bluntly dissect the subcutaneous tissue to create a subcutaneous tissue tunnel from the first incision to a second incision exiting from the abdomen spaced from the first incision;
10. the trocar is detached from the dialysis catheter leaving the catheter in place extending through the tissue tunnel between the first and second incisions; and
11. the second incision is closed and the dialysis catheter is left in place for the desired period of time.

Alternatively, in the prior art method the trocar tip can be attached to the distal end of the catheter, the catheter inserted through the second incision, and then tunneled to the first incision. The catheter is then inserted through the tear away sheath.

This multiple step process is time consuming and complicates the surgical procedure. This multiple step process also adds to the cost of the procedure, not only because of the additional surgeon's time but because additional components, such as the tear-away sheath, are required which increases the overall cost of the catheter system. Also, removal of the dilator increases the tendency of the sheath to kink causing difficulties in catheter insertion.

The use of the tear away sheath is also potentially problematic. The tear-away style sheath has lines of weakness to separate the sheath as it is pulled apart by the pull tabs to enable removal of the sheath. However, the sheath can potentially cause damage to the surrounding tissue as it is being pulled apart and can cause infection. Moreover, pulling the sheath laterally can enlarge the incision, thereby increasing the difficulty of closing the incision at the end of the procedure. Also, since the sheath is pulled in the proximal direction for removal, it could pull the catheter proximally as well, thereby pulling it away from the desired site, and requiring repositioning. The edges of the tear away can also lacerate the surgeon's glove and finger.

It would therefore be advantageous if a peritoneal dialysis catheter insertion method could be provided which reduces some of the foregoing procedural steps, thereby decreasing the complexity of the procedure and decreasing the hospital and surgeon costs. It would also be advantageous if such dialysis catheter insertion method could be provided which would be less traumatic and avoid the foregoing problems associated with the use of a tear-away sheath, such as trauma to the surrounding tissue, incision enlargement and dislodgement of the catheter.

Another area of dialysis catheter insertion which needs improvement is guiding the catheter to the target site. Dialysis catheters are composed of flexible tubing to minimize damage to the tissue during insertion and use. This flexibility, however, oftentimes results in kinking of the catheter. This kinking can adversely affect fluid flow. Also, the catheter needs to have some degree of stiffness to enable directing the catheter. The stiffness, however provides its own risks since if the catheter is not properly directed, the catheter can inadvertently be forced against and damage tissue. Several different approaches have been discussed in the prior art to increase stiffness of catheters such as providing a distal tip of stiffer material to guide the catheter as in U.S. Pat. No. 5,957,893, using materials of different durometers in various portions of the catheter (U.S. Pat. No. 5,348,536), placing an additional concentration of material in the tip as in U.S. Pat. No. 4,583,968, or providing reinforcing strips, obturators or tubes within the catheter body to increase the rigidity (e.g. U.S. Pat. Nos. 4,619,643, 4,950,259 5,221,255, 5,221,256, and 5,246,430). The need however exists to improve the balance between flexibility and stiffness. Thus it would be advantageous to provide a catheter with sufficient flexibility to accommodate curves while still having sufficient stiffness to enable guiding the flexible catheter tubing atraumatically through the subcutaneous tissue tunnel and into the abdominal cavity.

It is also desirable to provide the smallest catheter profile, i.e. the smallest outer diameter catheter body. This profile facilitates insertion and facilitates closure of the catheter incision. However, the desire for smaller diameter catheters must be balanced against the need for providing sufficient sized lumens to enable proper fluid flow. Also, a sufficient relationship must be maintained between the size of the lumens and the overall diameter of the catheter to maintain the structural integrity of the catheter.

The need therefore exists for an improved dialysis catheter which facilitates the dialysis procedure. Such catheter would advantageously reduce the catheter insertion time, simplify the catheter insertion process, eliminate the need for a peel-away introducer sheath, reduce unwanted kinking of the catheter during insertion, and strike an optimal balance between overall catheter and lumen size.

SUMMARY

The present invention overcomes the disadvantages and deficiencies of the prior art. The present invention provides a peritoneal dialysis catheter for insertion into the abdominal cavity of a patient for delivering and withdrawing fluid from a patient comprising a catheter body having a proximal portion, a distal tip portion and a first longitudinally extending lumen configured to deliver fluid into the abdominal cavity. First and second side openings are formed in an outer wall of the catheter body adjacent the distal tip portion and are in fluid communication with the first lumen and configured for passage of fluid therethrough. A stiffening insert is positioned in the distal tip portion and has a first stiffness greater than a second stiffness of the distal tip portion to facilitate entry in to the abdominal cavity. The stiffening insert has a lumen therethrough communicating with the first lumen.

The catheter body is preferably flexible. In one embodiment at least a distal section forms a coil (spiral) shape within the abdominal cavity of a patient. The first and second side openings are preferably positioned proximally of the stiffening insert. The distal tip portion preferably has a bullet nose configuration and an internal shoulder providing a stop for a stiffening member inserted through the lumen of the catheter body.

The catheter preferably further comprises a stiffening member removably positionable within the lumen and including a lumen for receiving a guidewire therethrough. The stiffening member is preferably mountable to the proximal portion of the catheter, whereby torquing the stiffening member places the catheter body in tension to stretch the catheter body, thereby reducing at least a portion of the outer diameter during insertion.

The present invention also provides a catheter for delivering and withdrawing blood from a patient's body comprising a flexible catheter body having an outer wall, a distal portion, a lumen extending from a proximal portion of the catheter body to the distal portion and configured to receive a guidewire therein and to allow blood passage therethrough, and a distal section having a coil shape. At least two side openings are formed in the outer wall of the catheter body wherein each side opening is in fluid communication with the lumen. A stiffening member having a lumen for receiving a guidewire therethrough is removably positionable within the lumen of the catheter body and mountable to a proximal portion of the catheter, terminating proximally of a distalmost tip of the catheter body.

Preferably, the stiffening member has a threaded portion on a proximal end portion for mounting the proximal end of the stiffening member to the catheter and for torquing the stiffening member to stretch the catheter body. In one embodiment, the stiffening member has a threaded portion at its distal end portion for mounting to the catheter body. In another embodiment, the stiffening member has an abutment tip for abutting a shoulder formed internally in the distal tip portion of the catheter body.

The present invention also provides a system for placement of a dialysis catheter comprising a dilating trocar and a dialysis catheter having a coiled distal end section. The trocar has a housing at a proximal end portion, an elongated tubular portion extending from the housing, and a lumen extending longitudinally through the housing and tubular portion. The tubular portion terminates in a blunt dissecting tip configured to dilate tissue and create a subcutaneous tissue tunnel. The lumen has a first internal diameter and is configured to removably receive a guidewire therethrough for over the wire insertion of the trocar. The dialysis catheter has a first longitudinally extending lumen and a plurality of side lumens in communication with the longitudinally extending lumen. At least a portion of the catheter has an outer diameter configured for insertion through the subcutaneous tissue tunnel and the longitudinally extending lumen is configured to receive the guidewire for over the wire insertion of the dialysis catheter through the tissue tunnel when the trocar is removed. The distal section forms a coiled shape when the catheter is positioned within the body.

A method of inserting a peritoneal dialysis catheter into the abdominal cavity of a patient is also provided comprising:

inserting a guidewire and needle through a first incision into the abdominal cavity of a patient;

providing a trocar having a lumen and a dissecting tip;

inserting the trocar through a second incision in the patient and advancing the trocar towards the first incision to create a subcutaneous tissue tunnel;

threading the guidewire through the lumen of the trocar so the guidewire extends through the second incision;

removing the trocar;

providing a dialysis catheter having a lumen for passage of fluids; and inserting the dialysis catheter over the guidewire through the second incision, through the subcutaneous tunnel and into the abdominal cavity.

The method may further comprise the step of temporarily inserting a stiffening member in the lumen of the catheter to facilitate insertion of the catheter. The step of inserting the stiffening member may include the steps of twisting the stiffening member and securing the stiffening member to a proximal portion of the catheter to stretch the catheter to reduce at least a portion of the outside diameter of the catheter.

The present invention also provides a method of inserting a peritoneal dialysis catheter over a guidewire into the abdominal cavity of a patient comprising:

inserting a guidewire through a first incision in a patient;

manipulating the guidewire to extend out of a second incision of the patient's body;

providing a dialysis catheter having a lumen with a distal and proximal opening;

inserting the guidewire through the lumen and advancing the dialysis catheter over the guidewire through the second incision in the patient's body;

advancing the dialysis catheter subcutaneously over the guidewire and into the abdominal cavity; and removing the guidewire leaving the dialysis catheter in place for a period of time.

The method may further comprise the step of inserting a stiffening member through the lumen in the dialysis catheter to help advance the dialysis catheter to the desired site. The method may also further comprise the step of inserting an introducer needle through the first incision for placement of the guidewire.

BRIEF DESCRIPTION OF THE DRAWINGS

Preferred embodiment(s) of the present disclosure are described herein with reference to the drawings wherein.

DETAILED DESCRIPTION OF PREFERRED EMBODIMENTS

Turning now to the drawings, wherein like reference numeral identify similar or like components throughout the several views, a peritoneal dialysis catheter system is provided for over the wire insertion into the abdominal cavity. The catheter system includes a flexible catheter, a guidewire, and a trocar for creating a tissue access tunnel for the catheter and for pulling the guidewire through the tunnel for guiding the catheter.

More specifically, and referring first to FIGS. 5–6 and 10–12, catheter 10 has a catheter body or catheter tube 11 having a distal end portion 31, a proximal end portion 33, and an intermediate portion 35. Distal portion 31 terminates in nose 32 which is illustratively substantially conical in shape. Proximal end portion 33 includes hub 12, where the lumen formed within catheter tube 11 is connected, i.e. transition, to the respective inflow/outflow tube (not shown) to enable infusion and withdrawal of fluid for dialysis. A conventional tube clamp (not shown) is provided to cut off fluid flow through the inflow/outflow tube as desired. As used herein, the terms "inflow" and "outflow" refer to the direction of fluid flow with respect to the patient's body such that "inflow" refers to fluid delivered to the body while "outflow" refers to fluid withdrawn from the body.

As shown, intermediate portion 35 of catheter 10 extends through subcutaneous tissue tunnel "t", and curves downwardly toward the target site, e.g. abdominal cavity This tunnel "t" secures the catheter in place for dialysis, with fibrous cuff 36 (FIG. 8) enabling tissue ingrowth. The formation of the tunnel "t" and the insertion of the catheter 10 therethrough will be discussed below in conjunction with the discussion of the catheter insertion method.

Figure 10:
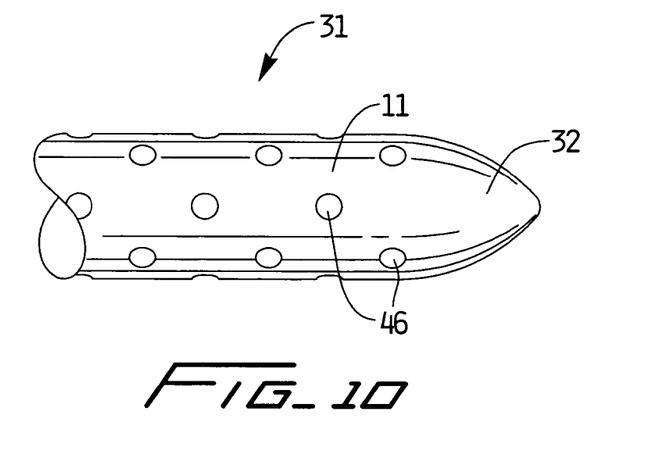
FIG. 10 is an enlarged view of the distal end of the dialysis catheter of FIG. 8 or FIG. 9.
Figure 11:
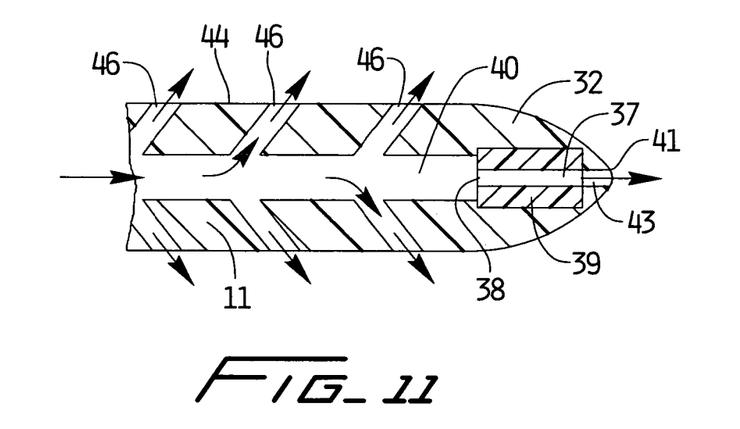
FIG. 11 is a cross-sectional view of the distal end of the catheter of FIG. 10 showing the introduction of dialysate fluid through the central lumen and side openings.

More specifically, and with reference to FIGS. 10 and 11, details of the catheter tip will now be described. Central longitudinal lumen 40 is formed within catheter tube 11, extends the entire length and is designed for transporting dialysate fluid to the patient's abdominal cavity and for removing the fluid and wastes from the cavity. Lumen 40 is also configured to receive a guidewire 20 to direct the catheter to the desired position. Lumen 40 extends through conical nose 32, transitioning into lumen 37 within stiffening insert 39, and terminating in distal opening 41.

This nose or distal tip 32, is composed of the same material as the catheter body 11 and has a stiffening insert 39 inserted through lumen 40 in the region of nose 32. The stiffening insert 39 is preferably composed of the same material as the catheter body 11 and nose 32, except it is made of a harder durometer material such as 72 shoreD vs. 85 shoreA for the catheter body 11. The material utilized can be, by way of example, polyurethane.

The stiffening insert 39, preferably cylindrical as shown, has lumen 37 longitudinally aligned with lumen 40 of catheter body 11, and in fluid communication beginning at region 38. Insert 39 engages the inner wall surface 44 of central lumen 40. Insert 39 includes either a stepped portion to provide an abutment surface (shoulder) 47 for stiffening rod 80 or internal threads (not shown) to mount stiffening rod 90 as described above. A guidewire extends through lumen 40 and lumen 37, exiting through distal opening 41 for over the wire insertion of catheter 10. The internal diameter of lumen 40 is reduced at region 43 to conform to the diameter of lumen 37.

Figure 12:
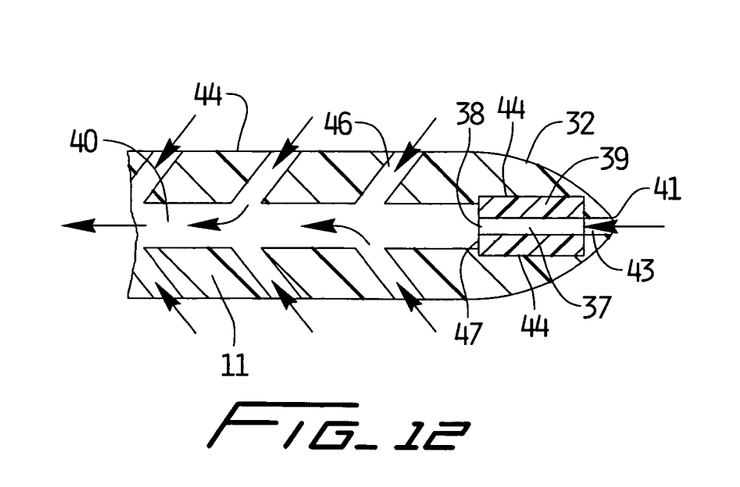
FIG. 12 is a cross-sectional view of the distal end of the catheter of FIG. 10 showing withdrawal of fluids through the central lumen and side lumen openings.

Lumen 37 of insert 39 thus communicates with central lumen 40 of catheter body 11 to deliver and withdraw fluid through distal opening 41. Additionally, proximal of stiffening insert 39 are side openings 46 formed through the outer wall 44 wall in fluid communication with lumen 40, also functioning to deliver and return fluid to the patient's body. Side openings or ports 46 are preferably angled outwardly as shown to facilitate delivery in the direction of blood flow. These additional openings help maintain the desired flow volume by distributing the fluid through multiple holes and by providing multiple suction holes for withdrawal of fluid. The arrows of FIGS. 11 and 12 schematically represent the dual direction of flow within catheter 10.

It is contemplated that additional or fewer openings can be provided and the openings can be axially displaced with respect to each other. Additional set(s) of openings can also be provided spaced proximally or distally from side openings 46.

One method of manufacturing this bullet shaped nose 104 is described and shown in provisional application No. 60/260,592, which as noted above, is incorporated herein in its entirety by reference. After formation of the cylindrical tube, stiffening insert 39 is placed within the central lumen at the distalmost end and substantially flush with the distalmost edge of the cylindrical tube. The tube is then formed into the bullet nose shape of FIG. 10 by a conventional radiofrequency or other heating process which allows the tip material to flow and form around the harder insert 39. After heating of the die and formation into this configuration, the material is cooled and thereby hardens to as the material fuses to the insert. A conventional core pin (not shown) can be used, during the forming process, which is withdrawn when the material hardens to maintain the opening.

It is also contemplated that the embodiments described in application Ser. No. 60/260,592 wherein the distal tip portion is composed of a different material than the other portions of the catheter body and is welded or attached by other means to the catheter body. The tip (nose), as described, can be composed of a stiffer material to facilitate tunneling and blunt dissection through tissue, or alternatively composed of a softer material, thereby being less traumatic upon contact with the tissue.

To facilitate insertion, the catheter 10 of the present invention is configured to receive a stiffening member in the form of a stiffening rod as described in application Ser. No. 60/260,592. The stiffening rod is inserted into central lumen 40 of catheter 10 and torqued to stiffen the flexible catheter for ease in over the wire insertion and navigation, and to reduce the outer diameter (profile) of the catheter body by stretching it during insertion. After placement of the catheter 10, the stiffening rod is removed, allowing the catheter to return to its higher profile position with the lumen of the necessary size for fluid transport to and from the body. Two embodiments of the stiffening rods are illustrated in FIGS. 13A and 13B.

Figure 13A:
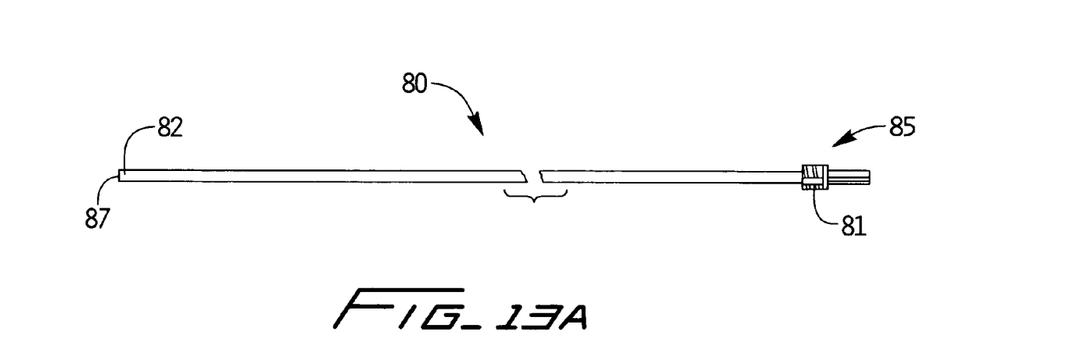
FIG. 13A is a side view of a first embodiment of a stiffening rod of the present invention to facilitate insertion of the dialysis catheter.

In the embodiment of the stiffening rod illustrated in FIG. 13A and designated generally by reference numeral 80, stiffening rod 80 has a distal tip 82, a proximal end portion 85 and an internal lumen extending therethrough. Stiffening rod 80 is inserted through the proximal end of inflow/outflow tube over the guidewire 20 (which extends through the lumen of the rod and through central lumen 40 of catheter body 11) until distal tip 82 abuts shoulder or stop 47 as mentioned above with respect to FIG. 12. The proximal end portion 85 of stiffening rod 80 has a threaded portion 81 which is screwed onto a screw thread of the tube. This temporarily secures the stiffening rod 80 within the catheter 10 during insertion. This threaded mounting requires the stiffening rod 80 to be manually twisted, thereby torquing rod 80 as it presses forwardly and applies a force against shoulder (abutment surface) 47 to stretch the catheter body 11 to reduce its outer diameter. This reduction in catheter body diameter or profile is described and shown in the aforementioned provisional application.

After the catheter 10 is positioned at the desired site, the stiffening rod 80 is unthreaded from the proximal thread of the inflow/outflow tube and removed from the central lumen 40 of the catheter 10 and from the tube, thereby allowing the catheter to return to its normal profile.

Figure 13B:
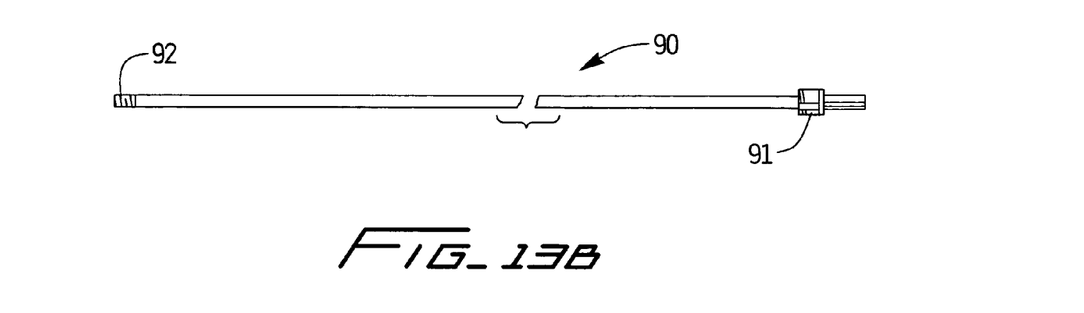
FIG. 13B is a side view of a second embodiment of a stiffening rod of the present invention.

An alternate embodiment of the stiffening rod is illustrated in FIG. 13B and designated generally by reference numeral 90. Stiffening rod 90 has a threaded distal end 92 which is threaded onto internal threads of the catheter. A series of proximal threads 91 are screwed onto the threads of the inflow/outflow tube in the same manner as described above for stiffener rod 80. The stiffening rod 90 functions in the same manner as stiffening rod 80, i.e. to stretch the catheter during insertion to reduce its profile and to stiffen it to facilitate insertion, the only difference being the mechanical threaded attachment of the distal end of the stiffening rod 90 to the catheter instead of the abutting relation of stiffening rod 80 with shoulder 47. Preferably, the distal threads 92 are first threaded onto the internal thread, followed by attachment of the proximal threads 91 as the stiffening rod 90 is torqued. Stiffening rod 90, like stiffening rod 80, is preferably circular in cross-section, although other configurations are also contemplated.

It should be appreciated that stiffening rod 80 and 90 can alternatively be temporarily attached at its proximal end by other means such as a bayonet lock, snap fit, etc. The rod could first be manually twisted and then mounted by these various means for retention in its torqued position.

The method of insertion of the catheter of the present invention provides an entire over the wire system. This is achieved by the provision of trocar 100 illustrated in FIGS. 3 and 4. Trocar 100 has a lumen formed thererethrough dimensioned for reception of guidewire 20. The lumen extends the entire length of trocar 100, from a proximal opening 106 in handle 108 to a distal opening on the underside of the trocar 100 or an axial opening 107 at the distalmost end. A distal opening can be formed just proximal of the distalmost tip, at the region where the trocar bends slightly upwardly, if a bent trocar is provided. Note the lumen of trocar 100 can be smaller than the outer diameter of the dialysis catheter. The blunt distal tip 102 of trocar 100 bluntly dissects tissue to create a subcutaneous tissue tunnel for subsequent securement of the catheter.

The method of insertion of the catheter will now be described in conjunction with FIGS. 1–6. The method will be described for inserting catheter 10, however it should be appreciated that other catheters described in the '592 provisional application can be modified for peritoneal dialysis and inserted in the same manner.

Figure 1:
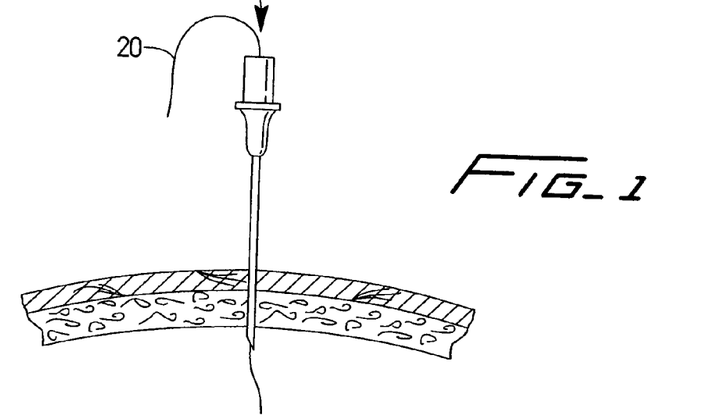
FIG. 1 is a side view showing insertion of the guidewire and introducer needle through a first incision and into the abdominal cavity.
Figure 2:
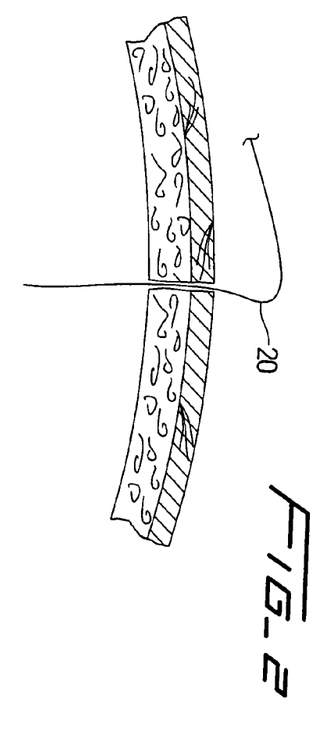
FIG. 2 is a side view showing the needle introducer removed leaving the guidewire in place in the abdominal cavity.

First, needle "N" and guidewire 20 are inserted through the abdominal cavity as shown in FIG. 1. The needle 'N" is then withdrawn, leaving the guidewire 20 in place, extending out of the patient's body at the proximal portion as shown in FIG. 2.

Figure 3:
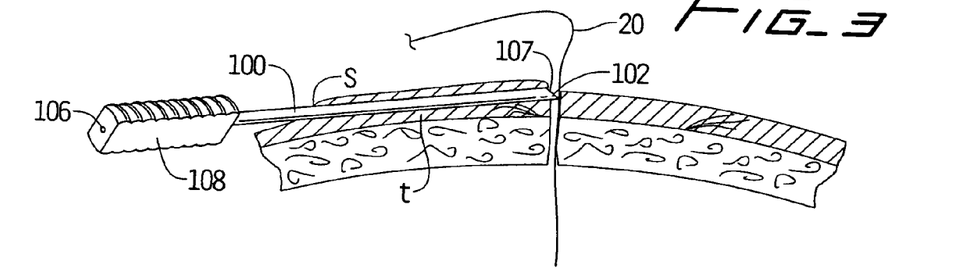
FIG. 3 is a perspective view illustrating a trocar being inserted through a second incision site and exiting at the first incision site to create a subcutaneous tissue tunnel.

Next, trocar 100 is inserted through a second incision "s" in the patient, bluntly dissecting and tunneling under the skin, and forced out of the tissue at the first incision or site, creating a tunnel "t" under the tissue as shown in FIG. 3. This provides a way to secure the catheter as described below.

Figure 4:
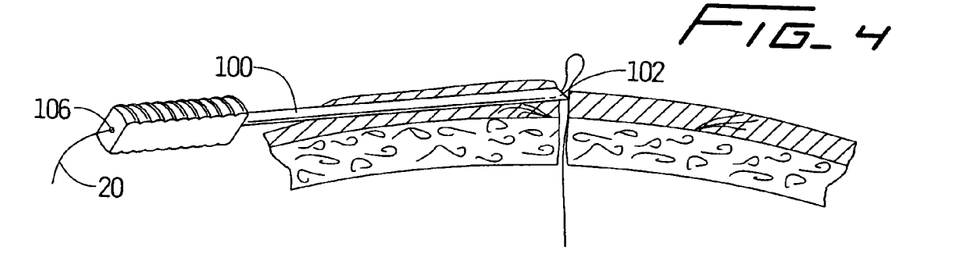
FIG. 4 is a perspective view illustrating the guidewire being threaded through the lumen of the trocar.
Figures 5, 6:
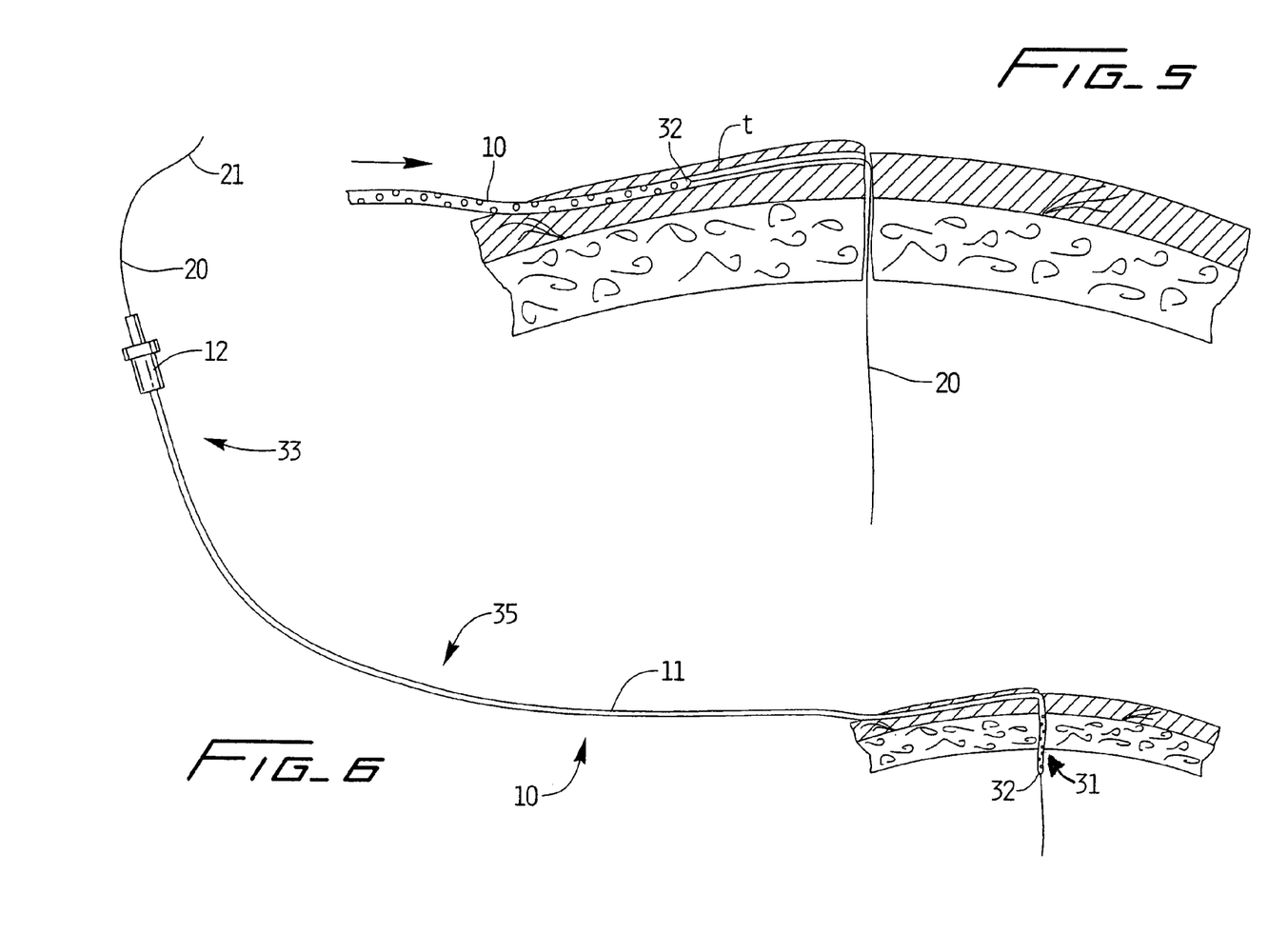
FIG. 5 is a side view illustrating the dialysis catheter of the present invention inserted over the guidewire through the tissue tunnel and advanced towards the first incision.
FIG. 6 is a side view illustrating a first embodiment of the dialysis catheter of the present invention extending through the tissue tunnel and first incision into the abdominal cavity of the patient.
Figure 7:
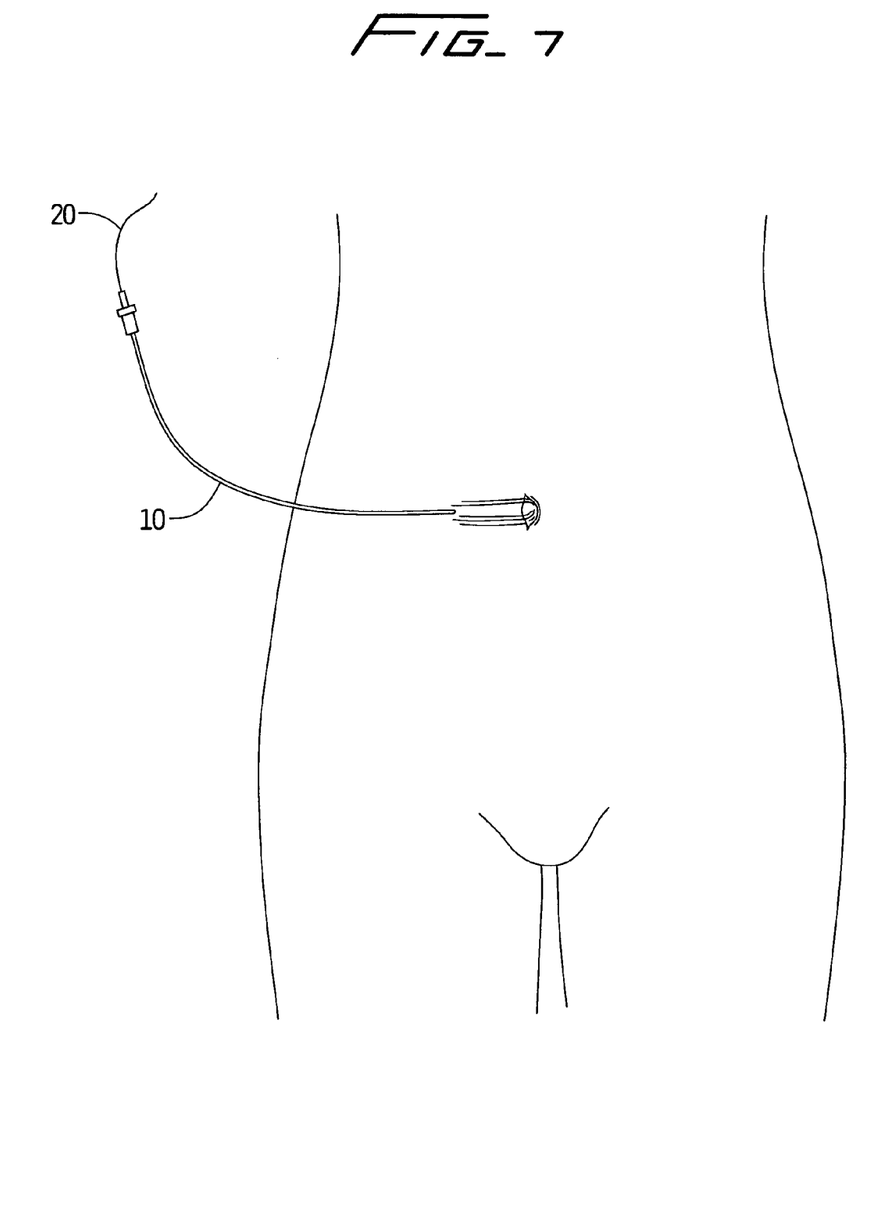
FIG. 7 is a top view showing the dialysis catheter positioned over the wire and extending into the abdominal cavity.

Guidewire 20 is then threaded through the central lumen of the trocar, with proximal portion first inserted through trocar distal opening 110 so it emerges out of proximal opening 106 as shown in FIG. 4. Trocar 100 is then withdrawn from the body in the direction of the arrow, leaving the guidewire 20 in place as shown. Thus, guidewire 20 extends from the abdominal cavity, through part of the first incision, through the tissue tunnel "t" and out through the second incision.

Figure 8:
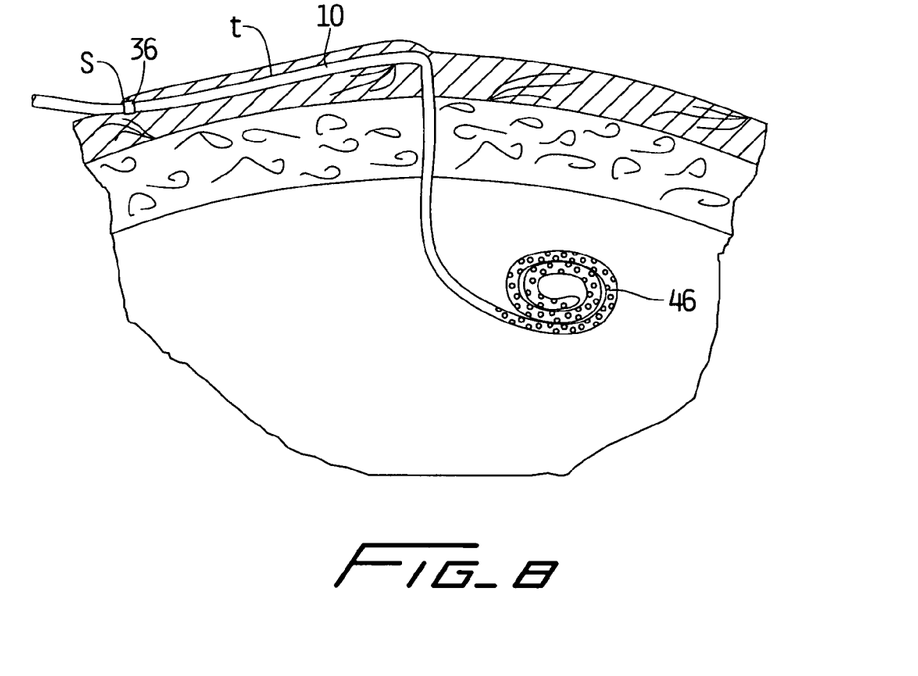
FIG. 8 is a side view illustrating the peritoneal wall in cross section and showing a coiled distal end of the first embodiment of the dialysis catheter within the abdominal cavity.

Catheter 10 is then threaded over the guidewire 20 (see FIG. 5), with the proximal portion 21 of the guidewire 21 first inserted through the distal opening of the catheter, and the catheter advanced distally so the guidewire extends through the length of the central lumen of the catheter, and through the hub 12. The catheter 10 is thus threaded over the wire, through the tissue tunnel "t" and into the abdominal cavity. The guidewire 20 is then withdrawn from the catheter in a proximal direction, leaving the catheter 10 in place for use as shown in FIG. 8. Note the stiffening member 80 or 90 (not shown for clarity) is preferably utilized, i.e. inserted over the guidewire 20 through the hub 12 and central lumen of the catheter to help guide the catheter 10 as described above.

Figure 9:
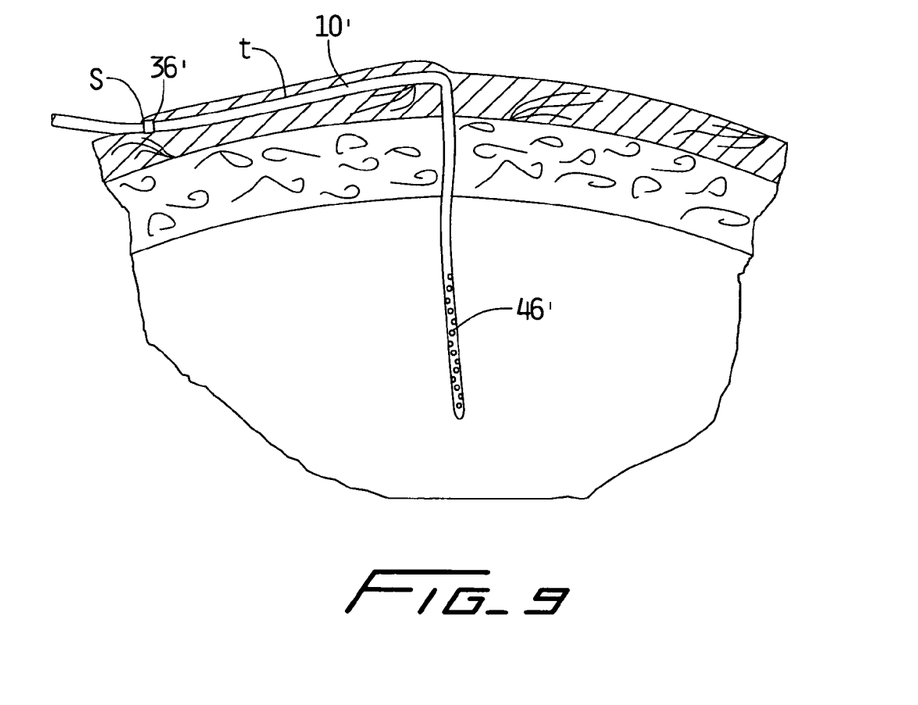
FIG. 9 is a side view illustrating the peritoneal wall in cross section and showing a straight distal end of a second embodiment of the dialysis catheter within the abdominal cavity.

In the embodiment of FIG. 8, the distal end of the catheter 10 is coiled. In the alternate embodiment of FIG. 9, a straight distal end catheter 10' is utilized, having a series of side openings 46'. One or more cuffs 36, 36' are positioned in the tissue tunnel "t" to aid in securement of the catheter by enabling tissue ingrowth over a period of time.

An alternative method can be utilized wherein the trocar creates a tissue tunnel from a second incision site, exiting a third incision site, adjacent the first incision site, and is then inserted through the first incision.

The present invention also contemplates the use of an alternative trocar for a partial over the wire system as described and shown in FIG. 22 in provisional application Ser. No. 60/260,592. As described, the partial over the wire system still eliminates the need for a tear way introducer sheath. In this method, the trocar is attached to the distal end of the catheter by insertion of barbed end into a mating fitting. Other means for temporarily attaching the trocar are also contemplated.

Trocar 100 can also be used in an alternate fashion wherein after the guidewire is placed in the cavity, and the trocar is tunneled through tissue, the guidewire is inserted through a distal hook or distal hole in the trocar, and the trocar is pulled proximally through the tunnel. Consequently, in this version, the guidewire is not threaded through a trocar lumen, but rather the trocar is utilized to pull (retract) the guidewire through the tissue tunnel. It should be understood that the trocar could have an eyelet, a hook or other means provided thereon for holding the guidewire to enable pulling the guidewire through the tissue tunnel.

The catheters described above can optionally include a surface treatment on the exterior and/or the interior. The surface treatments can include for example, an hydrophilic coating to increase lubricity and facilitate insertion, a drug coating such as heparin or containing IIb, IIIa inhibitors, inert coating substances such as Sorins carbon coating, and/or active coatings such as a silver ion coating.

It should be appreciated that although the catheter is described herein as a peritoneal dialysis catheter for dialysis, the catheter disclosed herein could have other surgical applications, such as drug delivery or blood sampling. Moreover, features of the catheter, tip configurations and lumen configurations can be utilized on other catheters.

While the above description contains many specifics, those specifics should not be construed as limitations on the scope of the disclosure, but merely as exemplifications of preferred embodiments thereof. Those skilled in the art will envision many other possible variations that are within the scope and spirit of the disclosure as defined by the claims appended hereto.

What is claimed is:

1. A peritoneal dialysis catheter for insertion into the abdominal cavity of a patient for delivering and withdrawing fluid from a patient comprising:

a catheter body having a proximal portion, a distal tip portion, and a longitudinally extending central lumen configured to deliver fluid into the abdominal cavity;

first and second side openings formed in an outer wall of the distal portion of the catheter body adjacent the distal tip portion, the first and second side openings being in fluid communication with the central lumen and configured for passage of fluid therethrough; and a stiffening member removably positionable within the central lumen and having a lumen for receiving a guidewire therethrough, wherein the stiffening member has a threaded portion on a proximal end portion for mounting the proximal end of the stiffening member to the catheter.

2. The catheter of claim 1, wherein the catheter body is flexible and at least a distal section is adapted to form a coil shape within the abdominal cavity of a patient.

3. The catheter of claim 2, wherein the distal tip portion has a bullet nose configuration.

4. The catheter of claim 1, wherein the distal tip portion includes an internal shoulder providing a stop for a stiffening member inserted through the first lumen of the catheter body.

5. The catheter of claim 1, wherein the stiffening member is mountable to the proximal portion of the catheter and terminates proximally of a distalmost tip of the catheter body.

6. The catheter of claim 5, further comprising third and fourth side openings in the outer wall spaced axially from the first and second side openings.

7. The catheter of claim 1, further comprising a stiffening insert positioned in the distal tip portion, the stiffening insert having a first stiffness greater than a second stiffness of the distal tip portion to facilitate entry in to the abdominal cavity, the stiffening insert having a lumen therethrough communicating with the first lumen.

8. The catheter of claim 5, wherein the catheter body is flexible and at least a distal section of the catheter is adapted to form a coil shape within the abdominal cavity of a patient.

9. The catheter of claim 4, wherein the catheter body is flexible and at least a distal section of the catheter is adapted to form a coil shape within the abdominal cavity of a patient.

10. The catheter of claim 1, wherein the stiffening member has an abutment tip for abutting an internal region in the distal portion of the catheter body.

11. The catheter of claim 7, wherein the first and second side openings are positioned proximally of the stiffening insert.

12. A peritoneal dialysis catheter for insertion into the abdominal cavity of a patient for delivering and withdrawing fluid from a patient comprising:
- a catheter body having a proximal portion, a distal tip portion, and a first longitudinally extending central lumen configured to deliver fluid into the abdominal cavity;
- first and second side openings formed in an outer wall of the distal portion of the catheter body adjacent the distal tip portion, the first and second side openings being in fluid communication with the central lumen and configured for passage of fluid therethrough; and
- a stiffening member removably positionable within the central lumen and having a lumen for receiving a guidewire therethrough, wherein the stiffening member is mountable to the proximal portion of the catheter and terminates proximally of a distalmost tip of the catheter body, wherein torquing the stiffening member places the catheter body in tension to stretch the catheter body, thereby reducing at least a portion of the outer diameter of the catheter body during insertion.

13. A catheter for delivering and withdrawing blood from a patient's body, the catheter comprising:
- a catheter body having an outer wall, a distal portion, a lumen extending from a proximal portion of the catheter body to the distal portion and configured to receive a guidewire therein and to allow blood passage therethrough, the catheter body being flexible and having a distal section having a coil shape;
- at least two side openings in the outer wall of the catheter body, each side opening being in fluid communication with the lumen; and
- a stiffening member removably positionable within the lumen of the catheter, the stiffening member mountable to a proximal portion of the catheter and terminating proximally of a distalmost tip of the catheter body, the stiffening member including a lumen for receiving a guidewire therethrough.

14. The catheter of claim 13, wherein the stiffening member has a threaded portion on a proximal end portion for mounting the proximal end of the stiffening member to the catheter and for torquing the stiffening member to stretch the catheter body.

15. The catheter of claim 13, wherein the stiffening member has a threaded portion at its distal end portion for mounting the distal end portion to the catheter body.

16. The catheter of claim 13, wherein the stiffening member has an abutment tip for abutting a shoulder formed internally in the distal portion of the catheter body.

* * * * *